(12) United States Patent
Pedersen et al.

(10) Patent No.: US 8,497,125 B2
(45) Date of Patent: Jul. 30, 2013

(54) PLURIPOTENT CELLS FROM THE MAMMALIAN LATE EPIBLAST LAYER

(76) Inventors: Roger Pedersen, Cambridge (GB); Ludovic Vallier, Cambridge (GB); Gabrielle Brons, Cambridge (GB)

( * ) Notice: Subject to any disclaimer, the term of this patent is extended or adjusted under 35 U.S.C. 154(b) by 0 days.

(21) Appl. No.: 13/437,989

(22) Filed: Apr. 3, 2012

(65) Prior Publication Data

US 2012/0238014 A1     Sep. 20, 2012

Related U.S. Application Data

(62) Division of application No. 12/312,395, filed as application No. PCT/GB2007/004302 on Nov. 9, 2007, now Pat. No. 8,153,423.

(30) Foreign Application Priority Data

Nov. 9, 2006    (GB) .................................. 0622395.2

(51) Int. Cl.
    *C12N 5/00*           (2006.01)
    *C12N 5/02*           (2006.01)

(52) U.S. Cl.
    USPC .......................................... 435/378; 435/325

(58) Field of Classification Search
    USPC .................................. 435/378, 325
    See application file for complete search history.

(56) References Cited

FOREIGN PATENT DOCUMENTS

WO    WO2006026473      3/2006

OTHER PUBLICATIONS

Ptaszek et al. Regulatory Networks in Stem Cells, Ed. Rajasekar, pp. 27-36, 2009.*
Cao et al. J. of Exp. Zoo., 311A: 368-376, 2009.*
Brevini et al. Theriogenology, 74: 544-550, 2010.*
Pads et al. Theriogenology, 74: 516-524, 2010.*
Chen et al., Exp Biol Med May 2006 vol. 231 No. 5 534-544.*
Lim et al., Proteonomics, 2: 1187-1203, 2002.*
Vallier. L., et al, J Cell Sci 2005; 118:4495-4509.
Daylin, J., et al, Development 2005; 132:1273-1282.
Beattie, G.M., et al, Stem Cells 2005; 23:489-495.
Brons, I.G.M., et al, Nature 2007; 448:191-195.
Tesar, P.J., et al, Nature 2007; 448; 196-199.

* cited by examiner

*Primary Examiner* — Thaian N Ton
(74) *Attorney, Agent, or Firm* — Linda O. Palladino; Gail M. Kempler

(57) ABSTRACT

The invention relates to the isolation and propagation of pluripotent cells isolated from the mammalian late epiblast layer, termed Epiblast Stem Cells (EpiSCs). These cells are useful in a range of applications, including the generation of transgenic animal species.

6 Claims, 2 Drawing Sheets

PLURIPOTENT CELLS FROM THE MAMMALIAN LATE EPIBLAST LAYER

This application is a divisional application of U.S. National Stage application Ser. No. 12/312,395, filed May 9, 2009 and claims priority under 35 USC §119 to International Application No. PCT/GB2007/004302, filed Nov. 9, 2007, which claims priority to Great Britain Application No. 0622395.2, filed Nov. 9, 2006, the contents of which are incorporated herein by reference in their entirety.

This invention relates to the production and culture of pluripotent mammalian cells.

While the first mouse embryonic stem cell (mESC) lines were derived 25 years ago (Evans, 1981, Martin, 1981) using feeder layer-based blastocyst cultures, subsequent efforts to extend the approach to other mammals, including both laboratory and domestic species, have been relatively unsuccessful. The most notable exceptions were the derivation of primate ES cell lines by Thomson and colleagues (Thomson, 1995, Thomson, 1996) followed shortly by their derivation of human ES cells (hESCs) (Thomson, 1998). Despite the similarity of hESC derivation methodology, undifferentiated proliferation and developmental pluripotency to the properties of mouse ESCs, early studies revealed basic differences between them. In addition to having distinct cell surface markers, hESCs were unresponsive to Leukaemia Inhibitory Factor (LIF), which is able to maintain mouse ESC pluripotency in serum-containing medium (Thomson, 1998, Daheron, 2004) and BMP4, which cooperates with LIF to maintain mESC pluripotency in serum-free conditions (Ying, 2003), induces rapid differentiation of hESC into extraembryonic cell types (Xu, 2002). Finally, it has recently been established (Vallier, 2004, Vallier, 2005, Beattie, 2005, James, 2005) that hESCs rely instead on Activin/Nodal and FGF (Xu, 2005, Levenstein, 2006) signalling pathways to maintain their pluripotent status.

The present inventors have isolated and propagated a previously unreported type of pluripotent cell, termed 'Epiblast Stem Cells' (EpiSCs). These cells are useful in a range of applications, including the generation of transgenic animal species.

One aspect of the invention provides a method of producing pluripotent cells from a mammal comprising:

culturing one or more mammalian late epiblast cells in a chemically defined medium in the presence of an activin agonist.

A pluripotent mammalian cell is an unspecialized cell that is capable of replicating or self renewing itself and developing into specialized cells of all three primary germ layers i.e. ectoderm, mesoderm and 5 endoderm but are not able to develop into all embryonic and extra-embryonic tissues, including trophectoderm (i.e. not totipotent). Pluripotent cells arise from the division of totipotent cells.

Mammalian late epiblast cells are cells of the embryo after its pluripotent cells have undergone cavitation to form a simple epithelial layer (the late epiblast layer) after implantation i.e. pre- or early gastrulation (e.g. mouse embryo 5.0-6.5 d.p.c). Suitable cells may be obtained by isolating the late epiblast layer of a mammalian embryo and, optionally, isolating one or more cells from said layer.

Preferably, the late epiblast cells are separated and/or isolated from extraembryonic cells. This may be performed using routine techniques. For example, the late epiblast layer of an embryo may be separated from extraembryonic tissues by microdissection. Microdissection may be performed in a suitable buffer (e.g. Cell Dissociation Buffer; Invitrogen) at 4° C. for 15-20 mins or Collagenase (Type IV, Gibco, 1 mg/ml) medium at room temperature for 5-15 mins to promote dissociation of the layers.

The mammal may be a human or a non-human mammal, for example a rodent (e.g. a guinea pig, a hamster, a rat, a mouse), a marsupial (e.g., an opossum), a canine (e.g. a dog), a feline (e.g. a cat), a porcine (e.g. a pig), a bovine (e.g. cattle), an ovine (e.g. sheep), a caprine (e.g. goat), an equine (e.g. a horse), a non-human primate, such as a simian (e.g. a monkey or ape), a monkey (e.g. marmoset, baboon) or an ape (e.g. orang-utan, gorilla, chimpanzee, gibbon).

A chemically defined medium (CDM) is a nutritive solution for 35 culturing cells which contains only specified components, preferably components of known chemical structure.

A suitable chemically defined medium may comprise a basal culture medium, such as IMDM and/or F12 supplemented with insulin, for example at 0.5 ug/ml to 70 ug/ml, transferin, for example at a concentration of 5 1.51-ig/ml to 150 ug/ml, 1-thiolglycerol, for example at a concentration of 45 uM to 4.5 mM and BSA (or PVA), for example at a concentration of 0.5 mg/ml to 50 mg/ml.

Suitable CDM include the CDM of Johansson and Wiles (1995) consisting of: standard IMDM/F12 base (Life Technologies Inc., Gaithersburg, Md., USA) 7 ng/ml insulin, 15 ug/ml transferrin, 2.5 g/ml BSA (or 0.1% PVA), 1% chemically defined lipid concentrate (Invitrogen), and 350 uM 1-thiolglycerol. Other suitable CDM may comprise 50% IMDM plus 50% F12 NUT-MIX, supplemented with 7 ug/ml of insulin, 15 ug/ml of transferrin, 450 uM of monothioglycerol and 5 mg/ml bovine serum albumin fraction V.

Media and ingredients thereof may be obtained from commercial sources (e.g. Gibco, Roche, Sigma, Europabioproducts). BSA may be replaced in CDM by Polyvinyl alcohol (PVA), human serum albumin, Plasmanate™ (human albumin, alpha-globulin and beta globulin: Talecris Biotherapeutics N.C. USA) or Buminate™ (human albumin: Baxter Healthcare), all of which are available from commercial sources.

Other suitable CDM which may be used in accordance with the present methods are known in the art (e.g. N12 medium).

An activin agonist is a compound which activates the Activin/Nodal signalling pathway, for example by binding to TGFbeta or activin receptors. Examples of activin agonists include activin A, activin B, activin AB, TGFbeta1, Growth and Differentiation Factor (GDF)-3, and Nodal.

Known activin receptors include heterodimers between type I activin receptors (ACVR1 GeneID: 90 NCBI reference NP_001096.1 GI: 4501895) and type II activin receptors (ACVR1B GeneID: 91 NCBI reference NP_004293.1 GI: 4757720 or ACVR1C GeneID: 130399 NCBI reference NP_660302.1 GI: 21687098).

Known TGFbeta receptors include heterodimers between type I TGFbeta receptors (TGFBR1 GeneID: 7046 NCBI reference NP_004603.1 GI: 4759226) and type II TGFbeta receptors (TGFBR2 GeneID: 7048 NCBI reference NP_001020018.1 GI: 67782326).

Activin A and activin B are dimeric polypeptides which exert a range of cellular effects via stimulation of the Activin/Nodal pathway, which is mediated by Smad 2 and Smad 3. Activin A is a homodimer of human activin A (NCBI GeneID: 3624 nucleic acid reference sequence NM_002192.2 GI: 62953137, amino acid reference sequence NP_002183.1 GI: 4504699) or activin A from another mammalian species. Activin B is a homodimer of human activin B (NCBI GeneID: 3625, nucleic acid reference sequence NM_002193.1 GI: 9257224 amino acid reference sequence NP 002184.1 GI:

9257225) or Activin B from another mammalian species. Activin AB is a heterdimer comprising activin A and activin B subunits. Activin A, B and AB are available commercially (e.g. SBH Sciences, Mass. USA).

Transforming growth factor, beta 1 (TGFbetal) may be human TGFbetal (GeneID: 7040 nucleic acid reference sequence NM_000660.3 GI: 63025221, amino acid reference sequence NP_000651.3 GI: 63025222) or TGFbetal from another mammalian species. TGFbetal is available commercially (e.g. Sigma-Aldrich).

Growth Differentiation Factor (GDF)-3 may be human GDF-3 (GeneID: 9573; nucleic acid reference sequence NM_020634.1 GI: 10190669; amino acid reference sequence NP_065685.1 GI:10190670) or GDF-3 from another mammalian species. GDF-3 is described, for example, in Chen et al Development (2006) 133 319-329.

Nodal may be human Nodal (GeneID: 4838 nucleic acid reference sequence NM_018055.3 GI: 38176152, amino acid reference sequence NP_060525.2 GI: 29568107) or Nodal from another mammalian species. Nodal is available commercially (e.g. Sigma-Aldrich).

Conveniently, the concentration of the activin agonist in the CDM may be from 1 to 100 ng/ml, preferably about 10 ng/ml.

The CDM may further comprise fibroblast growth factor 2 (FGF2) (e.g. human FGF2 NCBI GeneID: 2247, nucleic acid sequence NM_002006.3 GI: 41352694, amino acid sequence NP_001997.4 GI: 41352695) Human recombinant FGF2 is available from commercial suppliers (e.g. R&D, Minneapolis, Minn., USA).

Conveniently, the concentration of FGF2 in the medium may be from 1 to 100 ng/ml, preferably about 12 ng/ml.

Preferably, the cells are cultured in the absence of BMP4.

Mammalian late epiblast cells may be cultured using routine mammalian cell culture techniques, for example on fibronectin or fetal bovine serum (FBS) coated plates in the above medium. Methods and techniques for the culture of mammalian cells are well-known in the art (see, for example. Basic Cell Culture Protocols, C. Helgason, Humana Press Inc. U.S. (15 Oct. 2004) ISBN: 1588295451; Human Cell Culture Protocols (Methods in Molecular Medicine S.) Humana Press Inc., U.S. (9 Dec. 2004) ISBN: 1588292223; Culture of Animal Cells: A Manual of Basic Technique, R. Freshney, John Wiley & Sons Inc (2 Aug. 2005) ISBN: 0471453293, Ho W Y et al J Immunol Methods. (2006) 310: 40-52, Handbook of Stem Cells (ed. R. Lanza) ISBN: 0124366430). In preferred embodiments, EpiSCs may be passaged using collagenase and mechanical dissociation, in accordance with standard techniques.

Standard mammalian cell culture conditions may be employed, for example 37° C., 21% Oxygen, 5% Carbon Dioxide. Media is preferably changed every one day and cells allowed to settle by gravity.

EpiSCs may be further maintained and propagated in the medium.

EpiSCs produced as described above may be allowed to differentiate, for example into a lineage of one of the three germ layers; endoderm, mesoderm and neuroectoderm. For terminal differentiation, EpiSCs may be cultured in the absence of growth factors, for example in DMEM/2% B27 (Invitrogen) or CDM or other suitable media, which may also include combinations of established factors for the production of particular cell lineages.

For example, EpiSCs may be cultured in a chemically defined medium (CDM) supplemented with one or more differentiation factors and allowed to differentiate into partially differentiated progenitor cells or fully differentiated cells.

Differentiation factors include growth factors which modulate one or more of the Activin/Nodal, FGF, Wnt or BMP signalling pathways. Examples of differentiation factors include FGF2, BMP4, retinoic acid, TGFbeta, GDF3, LIF, IL and activin.

To produce progenitor cells of an ectoderm lineage, for example a neuroectoderm lineage, EpiSCs may be cultured in a chemically defined medium (CDM) supplemented with FGF2 and an Activin antagonist, such as SB431542 (Sigma, Tocris) or a soluble protein factor such as Lefty, Cerberus or follistatin, and allowed to differentiate into partially differentiated progenitor cells or fully differentiated cells. Fully differentiated cells may include neural cells such as neurons, and glial cells, such as astrocytes and oligodendrocytes.

To produce progenitor cells of a mesendoderm lineage (i.e. either mesoderm or endoderm lineages), EpiSCs may be cultured in a chemically defined medium (CDM) supplemented with Activin, FGF2 and BMP4, and allowed to differentiate into partially differentiated progenitor cells or fully differentiated cells.

Differentiated cells produced from EpiSCs may be useful in a range of applications, including drug screening, in vitro modelling, and transplantation.

Another aspect of the invention provides a pluripotent mammalian cell produced or obtainable by a method described herein.

Pluripotent mammalian cells (EpiSCs) produced by the present methods have a number of characteristic features. For example, EpiSCs express specific markers of the epiblast layer of the post-implantation embryo, such as FGF5 and Nodal, and do not express specific markers of the inner cell mass (i.e. blastocyte cells), such as GBX2 or Rexl and do not express markers of germ cells such as Blimpi, Stella, and alkaline phosphatase. EpiSCs also express the pluripotency markers Oct-4, Nanog and Sox2 are able differentiate into endoderm, mesoderm or neuroectoderm cells.

Unlike blastocyst-derived pluripotent cells, EpiSCs are unresponsive to Leukaemia Inhibitory Factor (LIF) and differentiate into extra-embryonic lineages in response to BMP4.

EpiSCs produced by the present methods may be substantially free from other cell types. In some embodiments, EpiSCs may be separated from other cell types using any technique known to those skilled in the art, including those based on the recognition of extracellular epitopes by antibodies and magnetic beads or fluorescence activated cell sorting (FACS) including the use of antibodies against extracellular regions of pluripotency markers such as SSEA-1.

As described above, pluripotent mammalian cells (EpiSCs) may be derived from a human or a non-human mammal, such as a mouse.

EpiSCs or ancestor cells thereof may be genetically manipulated, for example to reduce or silence expression of one or more genes or to express one or more heterologous polypeptide.

EpiSCs may be genetically modified during in vitro growth as described herein, for example by the introduction of a heterologous nucleic acid, such as a nucleic acid construct or vector, into the cells in the culture medium. This may be useful in expressing a marker or reporter gene or a therapeutic or other sequence of interest. For example, a heterologous protein may be over-expressed by stable transfection, expression of an endogenous gene may be knocked down or suppressed using SiRNA or knocked out using homologous recombination. Alternatively a reporter gene may be expressed using stable transfection or knock in by homologous recombination, or mutations may be generated using ethylnitrosourea (ENU) for mutant screening.

When introducing or incorporating a heterologous nucleic acid into an EpiSC, certain considerations must be taken into account, well known to those skilled in the art. The nucleic acid to be inserted should be assembled within a construct or vector which contains effective regulatory elements which will drive transcription in the target cell. Suitable techniques for transporting the constructor vector into the cell are well known in the art and include calcium phosphate transfection, DEAE-Dextran, electroporation, liposome-mediated transfection and transduction using retrovirus or other virus, e.g. vaccinia or lentivirus. For example, solid-phase transduction may be performed without selection by culture on retronectin-coated, retroviral vector-preloaded tissue culture plates.

Many known techniques and protocols for manipulation and transformation of nucleic acid, for example in preparation of nucleic acid constructs, introduction of DNA into cells and gene expression, and analysis of proteins, are described in detail in *Protocols in Molecular Biology*, Second Edition, Ausubel et al. eds. John Wiley & Sons, 1992 and *Molecular Cloning: a Laboratory Manual:* 3rd edition, Sambrook & Russell, 2001, Cold Spring Harbor Laboratory Press.

EpiSCs as described herein may be useful in the production of non-human mammals.

In some embodiments, an EpiSC may be injected into a blastocyst of said non-human mammal to produce a chaemeric embryo and the chaemeric embryo is then allowed to develop to term. The chaemeric embryo may be allowed to develop to term in its native mother or may be implanted into a surrogate to develop to term.

In other embodiments, EpiSCs may be aggregated with the embryo of a non-human mammal at the morula stage to produce a chaemeric embryo which is then allowed to develop to term. This may be achieved using standard techniques in the art. For example, EpiSCs may be aggregated. The zona pellucida may be removed from the embryo of the non-human mammal and an aggregate of EpiSCs added to the embryo. The embryo may then be cultured and allowed to develop into a chaemeric blastocyte. The chaemeric blastocyte may be allowed to develop to term in its native mother or may be implanted into a surrogate to develop to term.

In other embodiments, an EpiSC nucleus may be isolated and introduced into an unfertilised recipient mammalian egg cell, preferably a non-human mammalian egg cell. This may be useful, for example, in cloning non-human mammals or producing multipotent or pluripotent cells, for example embryonic stem or progenitor cells.

Suitable mammalian egg cells are arrested in the second metaphase of meiotic maturation.

Mammalian egg cells may be obtained from any suitable donor. Suitable egg cells may be collected from the reproductive tracts of ovulating animals using conventional surgical or non-surgical methods. Suitable egg cells may be matured in vitro using standard techniques from immature cells collected from the ovaries of a donor animal.

The egg cell nucleus may be removed or destroyed prior to introduction of the EpiSC nucleus (i.e. the egg cell may be enucleated), for example, by manually removing the nucleus with a micro-pipette, or by cautery. Alternatively, the egg cell nucleus may be removed after the introduction of the EpiSC cell nucleus.

The recipient egg cell may be from a different mammalian source to the EpiSC nucleus or, more preferably, from the same mammalian source.

Recipient egg cells containing an EpiSC nucleus may be cultured to generate populations of cells and cell lines, in particular pluripotent or multipotent cells and cell lines. Tissues, embryos and/or non-human animals may be generated from a population of said cells using techniques well known in the art (Wakayama et al (2001) Science 292; 740-743).

Following introduction of the EpiSC nucleus, embryonic development may initially be in vitro and subsequently in a surrogate. Thus, the egg cell may be initially cultured in vitro to produce a blastocyst or embryo and then the embryo may be transferred to a surrogate for subsequent development into a non-human mammal. Alternatively, embryonic development may be in vivo and the cell may be implanted into a surrogate directly after the EpiSC nucleus is introduced. The generation of non-human embryos and mammals from implanted nuclei is now well established in the art (Campbell K H, et al. (1996) Nature. 380:64-66, Wilmut I et al. (1997) Nature (London) 385:810-813, 'Principles of Cloning' Ed: Jose Cibelli et al ISBN 0-12-174597-X).

Transgenic non-human animals produced as described herein may be useful as models for disease conditions or as sources of tissue for xenotransplantation.

Another aspect of the invention provides a method of producing or expanding a population of pluripotent mammalian cells comprising:

culturing one or more pluripotent mammalian cells in a chemically defined medium in the presence of an activin agonist and, optionally FGF2, thereby producing or expanding the population of said cells.

Populations of pluripotent mammalian cells which may be produced or expanded in this way include human embryonic stem cell (hESCs) and Epiblast stem cell (EpiSCs) populations.

The population of pluripotent mammalian cells may predominately express Oct-4, Sox2 and Nanog, for example, at least 70%, at least 80% or at least 90% of the cells in said population may express one or more, two or more, three or more or all four of these markers. Human pluripotent cells may also express Tra-1-60, and SSEA-3 and mouse pluripotent cells may also express SSEA-1.

The cells may be cultured using conventional cell culture techniques, as described above. Chemically defined media are described in more detail above and include Johannsen and Wiles CDM containing insulin, transferrin, defined lipids and Bovine or Human Serum Albumin (BSA).

Another aspect of the invention provides the use of a chemically defined medium supplemented with an activin agonist and, optionally, FGF2, in the culture of pluripotent mammalian cells, in particular pluripotent non-human mammalian cells.

Suitable media are described above.

Various further aspects and embodiments of the present invention will be apparent to those skilled in the art in view of the present disclosure. All documents mentioned in this specification are incorporated herein by reference in their entirety.

The invention encompasses each and every combination and sub-combination of the features that are described above.

Certain aspects and embodiments of the invention will now be illustrated by way of example and with reference to the figures described above and tables described below.

Figure 1:
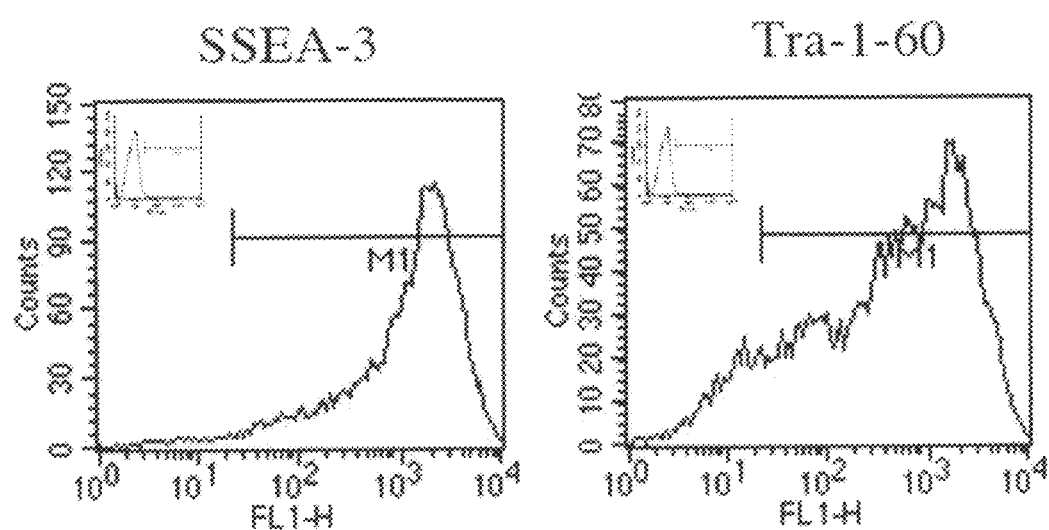
FIG. 1 shows that hESCs grown in CDM supplemented with Activin (10 ng/ml) and FGF2 (12 ng/ml) express homogenously pluripotency markers Tra-1-60 and SSEA-3. hESCs were grown for 85 passages (~250 days) in adherent conditions and then the fraction of pluripotent cells was established using FACS to detect expression of SSEA-3 (right panel) and Tra-1-60 (left panel).

Table 1 shows the efficiency of derivation of EpiSCs from rat and mouse embryos.

EXPERIMENTS

Material and Methods

EpiSC and hESCs culture in feeder free and serum free conditions.

For feeder and Serum free culture, hESCs (H9 and HI (WiCell, Madison, Wis.), hSF-6 (UCSF, San Francisco, Calif.)) and EpiSCs were grown in chemically defined medium (CDM), supplemented with Activin (10 ng/ml, RandD systems) and FGF2 (12 ng/ml, RandD systems). The composition of CDM was 50% IMDM (Gibco) plus 50% F12 NUT-MIX (Gibco), supplemented with 7 ug/ml of insulin (Roche), 15 ug/ml of transferrin (Roche), 450 uM of monothioglycerol (Sigma) and 5 mg/ml bovine serum albumin fraction V (Europabioproducts). Every 4 days, cells were harvested using 5 mg/ml collagenase IV (Gibco) or Accutase (BioWest) and then plated into plates (Costar) pre-coated with 15 ug/ml of human Fibronectin (Chemicon) for 20 minutes at 37 C and then washed twice in PBS.

RNA Extraction and Real Time PCR

Total RNAs were extracted from mouse ESCs or EpiSCs or their differentiated derivatives using the RNeasy Mini Kit (Qiagen). Each sample was treated with RNAse-Free DNAse (Qiagen) in order to avoid DNA contamination. For each sample 0.6 ug of total RNA was reverse transcribed using Superscript II Reverse Transcriptase (Invitrogen).

Real time PCR reactions mixture were prepared as described (Promega) then were denatured at 94° C. for 5 minutes and cycled at 94° C. for 30 seconds, 60° C. for 30 seconds, and 72° C. for 30 seconds followed by final extension at 72° C. for 10 minutes after completion of 35 cycles. Primer sequences were designed using the primer bank web software (http://pga.mgh.harvard.edu/primerbank/).

Immunofluorescence hESCs, mouse ESCs or EpiSCS were fixed for 20 minutes at 4° C. in 4% paraformaldehyde (PFA) and then washed three times in PBS. Cells were incubated for 20 minutes at room temperature in PBS containing 10% goat serum (Serotec) and subsequently incubated over night at 4° C. with primary antibody diluted in 1% goat serum in PBS as follows: SSEA-3 (1:100, Santa Cruz), SSAE-1 (1:25, gift from PW Andrews), Tra-1-60 (1:100, Santa CruZ), Oct-4 (1:100, SantaCruz), Sox2 (1:100, Abeam abI5830), Nanog (1:100, Abeam), Blirnpl (Abeam). Cells were then washed three times in PBS and incubated with fluorescein-Isothiocyanate-conjugated anti-mouse IgG or IgM (Sigma 1:200 in 1% goat serum in PBS) or rat IgM (Jackson laboratory 1:300 in goat serum in PBS) or rabbit IgG (Jackson laboratory 1:200 in donkey serum in PBS) for two hours at room temperature. Unbound secondary antibody was removed by 3 washes in PBS. Hoechst 33258 was added to the first wash (Sigma 1:10000).

Microarray Methods

RNA extraction and cDNA labelling: Total RNAs were extracted from mouse ESCs (B6xCBA)FI passage 15, EpiSCs (B6xCBA)FI passage 15, pure epiblast layer dissected from embryo at 5.5 d.p.c. or mouse blastocyst (B6xCBA)FI were extracted amplified and labelled as described by Tietjen et al.

Microarray data processing: Sample RNA was hybridized to Affymetrix (mg-u74Av2/hg-ul33+2) GeneChips®. All sample arrays were background corrected, normalized and summarized using default parameters of the RMA model2. Array processing was performed using the affy package of the Bioconductor (http://www.bioconductor.org) suite of software for the R statistical programming language (http://www.r-project.org).

The resulting data sets contained processed gene expression values for 54675 probe-sets (Affymetrix hg-u133+2 chip)/12488 probe-sets (Affymetrix mg-u74Av2 chip).

Analysis of Differential Regulation: The moderated t-statistic of Smyth et al, implemented in the Limma package of Bioconductor, was employed to assess the significance of differential gene (probe-set) expression between sample groups. In order to reduce errors associated with multiple hypothesis testing on such a scale, the significance 10 p-values obtained were converted to corrected q-values using the FDR method of Storey et al. Probe-sets with associated $q<0.01$ (FDR 1%) were deemed to exhibit significant differential expression between sample groups.

Data Visualisation: Heat maps of gene expression were created by importing relevant subsets of RMA processed microarray gene expression data into the dChip vl.3 microarray analysis package (http://www.biostat.harvard.edu/complab/dchip/). The dissimilarity between two microarray expression profiles of equal length was assessed with a bounded distance measure of [1.0—Pearson correlation] and displayed using multidimensional scaling (MDS) plots.

Teratomas

H9 cells or EpiSCs (B6xCBA)FI were harvested mechanically immediately prior to implantation and approximately $10^5$ cells were inoculated beneath the testicular capsule 7 of C.B.-17/GbmsTac-scid-bgDF N7 mice age 6 weeks (M&B, Denmark). The mice (5 per group) were sacrificed after 60 days and then the injected testes were cut into equal pieces using a razor blade. The material was fixed overnight in 4% neutral buffered formaldehyde, and dehydrated through a graded series of alcohols to xylene. The tissue was embedded in paraffin and serially sectioned at 5 um followed by characterization. Normal non-injected testes served as controls.

Results

Chemically defined culture conditions for growing hESCs in the absence of serum and feeders were developed using the chemically defined medium (CDM) of Johannsen and Wiles {Johansson, 1995 ttl32} containing insulin, transferrin, defined lipids, Bovine Serum Albumin (BSA) to which we added Activin 10 ng/ml, FGF2 12 ng/ml. H9, HI and hSF-6 hESCs grown on human fibronectin coated plates in CDM+ Activin+FGF (CDM/AF) over prolonged periods were assessed for expression of pluripotency markers by immunofluorescence and found to maintain the expression of the pluripotency markers Oct-4, Sox2, Tra-1-60, and SSEA-3. FACs analyses showed that the fraction of hESCs expressing the cell surface antigens Tra-1-60 and SSEA-3 were maintained at 95% and 87% after 85 passages in these culture conditions (FIG. 1).

Karyotype analyses showed that hESCs remained genetically stable and maintained a normal karyotype under these conditions. In addition, DNA methylation and monoallelic expression of imprinted genes remained normal, suggesting that they did not undergo any epigenetic alterations. Finally, teratomas from H9 cells were grown in CDM/AF. Approximately $5\times10^6$ H9 hESCs grown for 40 passages in CDM/AF were injected in the testis capsule of SCID-beige mouse and the resulting tumors were harvested 3 months after injection and assessed. hESCs thus cultured were found to be capable of forming teratomas when transplanted in immunodeficient mice confirming the pluripotent status of the cells.

Together, these results definitively demonstrate that hESCs can be grown in chemically defined condition (CDM/AF on Fibronectin coated plates) for long periods without losing their genetic or epigenetic 30 integrity or their pluripotency.

Similar culture conditions were tested for derivation of pluripotent cells from pre- and post-implantation rodent embryos. Entire mouse blastocysts grown in CDM/AF never gave rise to pluripotent cell lines (Table 1) showing that these culture conditions are not suitable for growing blastocyst derived embryonic stem cells. For derivation at post implantation stages, the late epiblast layer of embryos at pre- or early gastrulation stages (5.5 dpc or 6.5 dpc) was separated from extraembryonic tissues by microdissection using Cell Dissociation Buffer (Invitrogen) at 4° C. for 15-20 min. to promote dissociation of the layers. The resulting pure epiblast cell layers were then cultivated on fibronectin or fetal bovine serum (FBS) coated plates in CDM supplemented with 20 ng/ml of Activin A and 12 ng/ml of FGF2. After 24 hours, the epiblast layers formed colonies of compact cells having a high nucleo-cytoplasmic ratio, a characteristic morphological trait of pluripotent embryonic stem cells. Cells on the edge of the colony started to differentiate the following day, thereby producing a broad ring of stromal cells surrounding smaller aggregates of compact cells. These heterogeneous populations proceeded to form larger colonies of cells 4-5 days later. The latter colonies were picked, dissociated into smaller clumps using collagenase IV (Invitrogen) and then transferred to new dishes. Resulting colonies were passaged again 5 days later using collagenase and mechanical dissociation. Immunostaining analyses carried out after 20 passages showed that the colonies of compact cells expressed the pluripotency markers Oct-4, Nanog and SSEA-1. These cells were designated Epiblast Stem Cells (EpiSCs) on the basis of their origin from pure epiblast cell layers.

The expression of pluripotency markers Oct-4, Nanog and SSEA-1 was analysed in mouse ESCs of 129 strain grown on feeders in medium containing FBS and LIF and in mouse EpiSCs of the NOD genetic background and in rat EpiSCs of the Wistar strain grown for prolonged periods in CDM supplemented with Activin (and FGF2 for mEpiSCs) using immunoflurescence. Once established, EpiSC cells could be maintained for more than 40 passages while maintaining their expression of Oct-4, Nanog, Sox2 and SSEA-1. The success rate of derivation was 83% for (B6xCBA)FI and 90% for the NOD genetic background (Table 1), the latter being particularly challenging for the derivation of mESCs (Brook, 2003). Interestingly, EpiSCs grew as flat, compact colonies similarly to hESCs cultivated under the same culture conditions, and were distinct from mESCs, which form rounded, rather than flattened, colonies. In addition, passaging of single cell EpiSCs using trypsin or other single cell dissociation methods induced cell death or differentiation as typical for hESCs (and contrary to mouse ES cells), showing a low efficiency of clonal growth.

Dissected mouse epiblasts were grown in CDM supplemented with BMP4 (50 ng/ml) and LIF, two growth factors required to maintain the pluripotent status of mouse ESCs. After 24 hours, epiblast colonies grown in these conditions contain large number of cells with pluripotent-like morphology (high nucleocytoplasmic ratio, etc. However, all these cells had differentiated by the fourth day and they had formed complex tissues by the following day. We were not able to derive any EpiSC lines in the presence of LIF or/and BMP4.

Rat EpiSCs were grown in CDM supplemented in the presence of Activin (10 ng/ml), SB431542 (10 uM), BMP4 10 ng/ml+SB431542 (10 uM) or Activin (10 ng/ml)+Noggin (100 ng/ml). After one week, the expression of the pluripotency marker Oct-4 was analysed using immunostaining. Inhibition of Activin signalling by SB431542 was found to result in the loss of Oct-4 expression, and the addition of BMP4 was not able to rescue the pluripotent status of EpiSCs. Addition of the natural BMP inhibitor Noggin did not decrease expression of Oct-4. Similar results were obtained with mouse EpiSCs. Thus, inhibition of Activin/Nodal signalling using the Activin receptor inhibitor SB431542 induced rapid differentiation of EpiSCs, showing that, similarly to hESCs, EpiSC pluripotency depends strictly on Activin/Modal signalling.

Finally, EpiSCs could be derived in CDM supplemented with Activin alone (Table 1), indicating that FGF was not strictly required during this process. However, the presence of FGF improved the overall quality of the cultures, suggesting that its function consists in reinforcing the efficiency of Activin signalling, as in hESCs (Vallier, 2005). Taken together, these observations show that EpiSCs share with mouse ESCs the expression of standard markers of pluripotency but differ significantly from mouse ESCs in other features which are nevertheless shared with hESCs.

To examine the possibility that EpiSCs are related to germ cells, expression of specific germ cell markers were analysed by immunostaining and RT-PCR. EpiSC were found not to express Blirnpl, which is the first gene known to be expressed in allocated precursors of primordial germ cells (PGCs) just before gastrulation (Vincent, 2005, Ohinata, 2005). Also, EpiSCs were found to lack alkaline phosphase activity, a specific marker of primordial germ cells (PGCs) in the gastrulating embryo (De Felici, 1982). Importantly, EpiSCs did not express Stella, which is expressed in the ICM before implantation, in migrating PGCs at post-gastrulation stages and in EGs as well as in mouse ES cells (Payer, 2003). Moreover, when EpiSCs were derived from embryos carrying a GFP transgene under the control of the endogenous Stella promoter (Payer, 2006), GFP expression was not observed, thereby confirming the absence of Stella expression. Taken together, these results demonstrate that the pluripotent status of EpiSCs cannot be attributed to a PGC origin.

Figure 2:
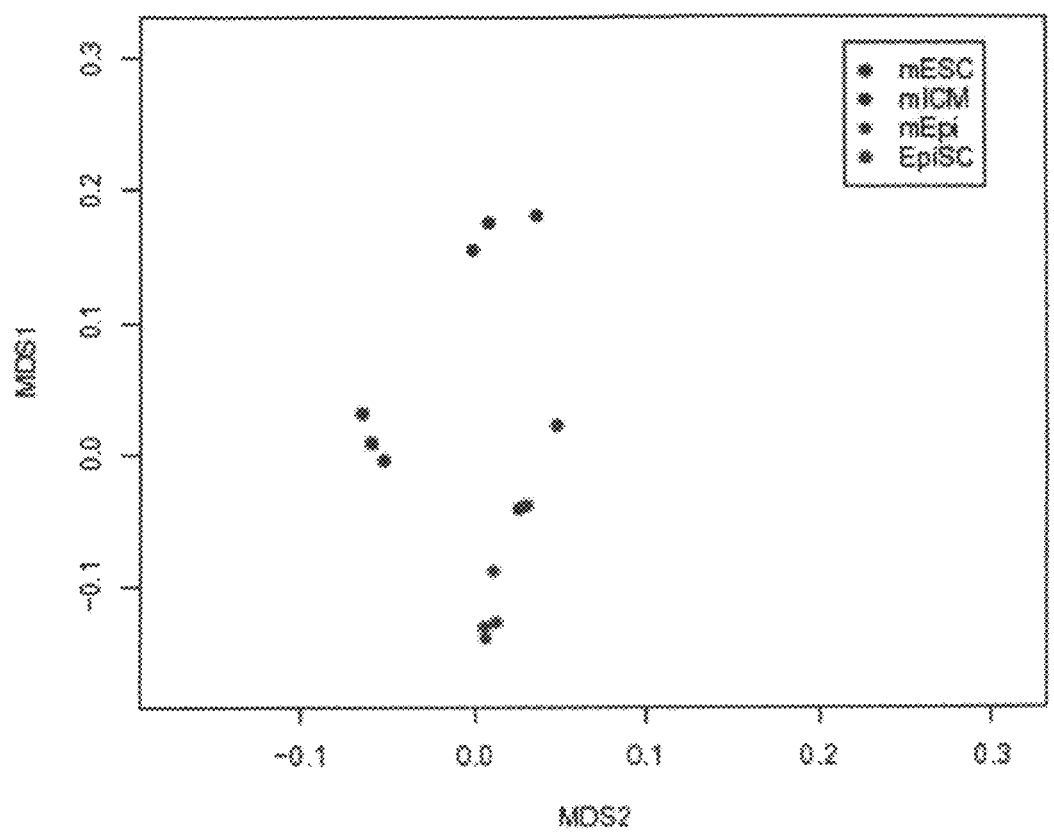
FIG. 2 shows a comparison of expression profile of ICM from embryos at the blastocyst stage, late epiblast from embryos at post implantation stages, mESCs and mEpiSCs, using MDS plot.

To further define the origin of EpiSCs, we performed a global analysis of the expression profile of pluripotency markers specific for pre- and post-implantation embryonic stages in 3 mouse EpiSC lines (passage 25) of the (B6xCBA) FI genetic background and in 2 mouse EpiSC lines (passage 15) of the NOD genetic background, using micro-array techniques. The resulting data were then compared to the expression profile of ICM from blastocyst embryo, late epiblast from post-implantation embryos, and two mESC lines (RI passage 14 and CGR8 passage 25) using MSD plot analysis (FIG. 2). This comparison showed that mEpiSCs express more common genes with Epiblast than with ICM or mESCs confirming that mEpiSCs share similarities with their embryonic equivalent. These observation was confirmed by RT-PCR analyses showing that EpiSCs did not express GBX2 or Rexl, two specific markers of the ICM (Pelton, 2002) that are silenced in early epiblast cells just after implantation but are expressed in mESCs and that transcripts coding for FGF5 (absent in mESCs) and Nodal, two genes specifically expressed in the late epiblast layer (Pelton, 2002) after implantation, were clearly detected in EpiSCs. These results provide indication that EpiSCs correspond closely to cells of the late epiblast layer of the intact post implantation mouse embryo, from which they had been derived.

To document further the pluripotent status of EpiSCs, we determined their capacity to differentiate into a wide variety of cell types in vitro and in vivo. Differentiation in vitro was achieved by growing EpiSC colonies for 5 days in non-adherent conditions in a medium supplemented with 20% Foetal Bovine Serum. The resulting embryoid bodies (EBs) were plated back onto plastic dishes and then grown for an additional 20 days. We analysed the expression of markers specific for the derivatives of the three primary germ layers every five days using RT-PCR. Expression of the pluirpotency marker Oct-4 had disappeared after 5 days, confirming that EpiSCs lost their pluripotent status in culture conditions favouring differentiation. Generation of mesodermal germ layer derivatives was confirmed by the expression of Brachyury, MixII (early mesoderm), MyoD, MyF5 (myogenic tissues) and Pecami (vascular tissues). The presence of beating EBs was also observed; confirming the presence of EpiSC derived cardiac cells. Generation of endoderm germ layer derivatives was confirmed by expression of SoxI7 and FoxA2 which was observed after 5 days of differentiation, as well as expression of Gata4, Gata6, aFP (liver), PdxI (pancreatic) and Cdx2 (gut) marker genes. Finally, expression of specific markers of neuronal differentiation (Sox2, Six3, NeuroDI, Islet 1 and p-tubulin III) was also detected. Together, these results demonstrate that EpiSCs were capable of differentiating into derivatives of all three primary germ layers in vitro.

To validate their pluripotency in vivo, EpiSCs colonies were injected in the testis capsule of immunodeficient mice and the resulting 30 teratomas were dissected and sectioned 30 days later. H & E staining showed that the teratomas contained a wide variety of tissues, including muscle, cartilage, neuronal rosettes, liver and gut thereby reaffirming the multi-lineage pluripotency of EpiSCs.

Finally, the capability of EpiSCs to recapitulate normal in vivo development was examined by generating chimaeric embryos using blastocyst injection. For these experiments, Tau-GFP expressing (B6xCBA) FI EpiSCs were generated by stably transfecting the pTP6 vector using lipofectamine 2000 (Vallier, 2004). In the first experiment injected embryos were recovered at 9.5 dpc by dissection, which revealed the presence of GFP expressing cells (1/17 dissected embryos). This chimaera displayed GFP expressing cells in all tissues examined, including liver, limb buds, brain and epidermis. A similar experiment was performed with NOD-EpiSCs and the injected embryos were allowed to develop to term. Two offspring out 20 embryos EpiSC injected blastocysts showed NOD chimaerism at a low level (−10%) by RT-PCR and another by coat colour; germ line transmission was not observed in 56 descendants from the coat colour chimaera. Together, these results show that EpiSC are capable of colonizing a blastocyst and differentiating into a large number of tissues in vivo following normal developmental pathways.

The relative inefficiency of chimaera formation could arise from the requirement to dissociate EpiSC colonies into single cells for the blastocyst injection procedure, thus reflecting their low efficiency of clonal growth. To address this possibility, mouse embryos at the morula stage were aggregated with EpiSC colonies, and the resulting chimaeras were transferred at the blastocyst stage to pseudopregnant mice. No chimaeric offspring were obtained using this approach, thus mirroring similar findings by Nagy and co-workers using mouse epiblast cells dissected from E 5.5 embryos. Taken together, these results provide indication that it is developmental asynchrony between EpiSCs and preimplantation embryos, rather than developmental potency, which limits their capacity to colonise the host embryo.

The hypothesis that Activin and FGF signalling in pluripotency are conserved in mammalian development is supported by the ability of Activin/Nodal signalling to maintain long-term pluripotency of both human ESCs and mouse EpiSCs. As a further test of this hypothesis, we attempted to derive EpiSCs from rats, a species from which embryonic stem cell derivation has been problematic. Following the method we established in the mouse, epiblast layers were dissected from rat embryos at pre-gastrula stages (E 7.5-8.5) and grown on fibronectin-coated or FBS coated plates in CDM supplemented with Activin and FGF. Contrary to the mouse, addition of FGF2 (or FGF4, EGF or HGF) induced differentiation of the early epiblast cultures, providing indication that the role of FGF in pluripotency maintenance is not as well conserved between mammalian species as that of Activin. Nevertheless, four EpiSC lines were derived out of 14 embryos of the Wistar strain and 1 EpiSC line was derived out of 20 embryos from the Sprague-Dawley strain using CDM supplemented with Activin alone.

Immunostaining showed that after 10 passages Rat EpiSCs expressed Get-4, Nanog and SSAE-4. Rat EpiSCs appear to share several key properties with mouse EpiSCs and hESCs, including low efficiency of clonal growth and strict dependence on Activin signalling. Rat EpiSCs were also capable of differentiating in vitro into neuron-like cells, rhythmically contracting cells and liver-like cells, suggesting similar potential for differentiation as mouse EpiSCs.

Together these results demonstrate that pluripotent stem cells can be cultured from widely separated species using chemically defined culture medium supplemented with Activin. On this basis we conclude that the Activin/Nodal pathway plays a central role in derivation and maintenance of a novel type of pluripotent stem cells from mammalian embryos, specifically representing the late epiblast cell population just before gastrulation.

Pluripotent embryonic stem cells had previously been obtained by culturing blastocysts or isolated ICMs of mouse and primate embryos. The data set out herein shows that pluripotent stem cell lines can also be generated from the late epiblast layer isolated after implantation (just before gastrulation), using Activin and FGF (mouse EpiSCs) in chemically defined culture conditions. Such EpiSCs can be grown extensively in vitro while maintaining their capacity to differentiate both in vitro and in vivo into a large variety of tissues, thereby demonstrating their pluripotent status.

EpiSCs differ from mouse ESCs not only in their embryonic origin but also by the signalling pathway maintaining their pluripotent status (Activin vs LIF), their expression profile, their low efficiency to colonise a blastocyst, and their low efficiency of clonal growth as isolated single cells. Importantly, EpiSCs express specific markers of the epiblast layer of the post-implantation embryo, including FGF5, and they lack the expression of specific markers of the ICM, including Rexl. In this regard they resemble the early primitive ectoderm-like (EPL) cells that were established by growing mouse ES cells in a 10 medium conditioned by the hepatic cell line HePG2 in the absence of LIF (Rathjen, 1999). However, EPL cells show some in vitro restriction from differentiation into neuroectoderm; in addition, LIF can revert EPL cells to ES cells. Neither of these two features is shared by EpiSCs. The lack of AP activity in EpiSCs and the absence of Blimpl expression also exclude the possibility of EpiSCs being related to PGCs. Consequently, EpiSCs represent a novel type of pluripotent embryonic stem cells sharing several characteristics with late epiblast cells in vivo.

The dependence of EpiSC pluripotency on Activin/Nodal signalling not only distinguishes them from mouse ESCs, but also highlights their resemblance to late epiblasts. Our results show that pluripotent stem cells of the late epiblast require only Activin/Nodal signalling to maintain their pluripotent status. The function of Activin/Nodal signalling in pluripotency is substantially conserved throughout mammalian evolution since hESCs and rat EpiSCs are also maintained by the Activin signalling pathway, thereby providing indication that EpiSCs could be derived from other species using this approach.

Besides their value for understanding basic mechanisms controlling early development, EpiESCs also offer a promising resource for transgenic alteration of the mammalian germline. Indeed, our success in deriving NOD mouse and rat EpiESCs provide indication that the protocol described here could be used to derive pluripotent cells in a wider range of mammalian species. Accordingly, EpiSCs could greatly facilitate the generation of transgenic livestock species, although the efficiency of EpiSCs in colonizing blastocysts was low. Nuclear transfer could represent an advantageous approach. Indeed, ESCs represent the best donor cells for nuclear reprogramming in the mouse (Meissner 2006) and the application of this approach to other species is largely limited by the absence of equivalent pluripotent cells. EpiSCs could represent a viable alternative for such purposes.

Lawson, K. A. et al. Ciba Found Symp 182, 68-84; discussion 84-91 (1994).
Vincent, S. D. et al. Development 132, 1315-25 (2005).
Ohinata, Y. et al. Nature 436, 207-13 (2005).
De Felici, M. & McLaren, A. Exp Cell Res 142, 476-82 (1982).
Payer, B. et al. Curr Biol 13, 2110-7 (2003).
Payer, B. et al. Genesis 44, 75-83 (2006).
Pelton, T. A. et al. J Cell Sci 115, 329-39 (2002).
Vallier, L. et al. Stem Cells 22, 2-11 (2004).
Rathjen, J. et al. J Cell Sci 112 (Pt 5), 601-12 (1999).
Nichols, J. et al Development 128, 2333-9 (2001).
Brook, F. A. et al. Proc Nati Acad Sci USA 94, 5709-12 (1997).
Conlon, F. L. et al. Development 120, 1919-28 (1994).
Gu, Z. et al. Development 126, 2551-61 (1999).
Gu, Z. et al. Genes Dev 12, 844-57 (1998).
Gardner, R. L. Ciba Found Symp 144, 172-81; discussion 181-6, 208-11 (1989).
Beddington, R. S. et al. J. Development 105, 733-7 (1989).

TABLE 1

| No. Epiblasts | | | | | | | Lines derived | | | | |
| --- | --- | --- | --- | --- | --- | --- | --- | --- | --- | --- | --- |
| | | Rat | | | | | | | Rat | | |
| Mouse | | | Sprague- | | | | Mouse | | | Sprague- | Rate |
| B6 | NOD | Wistar | Dawley | d.p.c. | Temp | Matrix | Growth factors | B6 | NOD | Wistar | Dawley | % |
| | 9 | | | 6.5 | 37° C. | fibro | Activin + FGF$_2$ | | 9 | | | 100 |
| 6 | | | | 5.5 | 37° C. | fibro | Acticin + FGF$_2$ | 5 | | | | 83 |
| | 5 | | | 6.5 | 37° C. | fibro | Activin + FGF$_2$ + Noggin | | 4 | | | 80 |
| | | ~14 | | 8.5 | 38° C. | FCS | Activin | | | 4 | | 35 |
| | | | ~20 | 8.5 | 37° C. | fibro | Activin | | | | 1 | 5 |

REFERENCES

Tietjen, I. et al. Neuron 38, 161-75 (2003).
Irizarry, R. A. et al. Nucleic Acids Res 31, el5 (2003).
Smyth, G. K. Stat Appi Genet Mol Biol 3, Article 3 (2004)
Storey, J. D. et al Proc Nati Acad Sci USA 100, 9440-5 (2003).
Kruskal, J. Psychometrika 29, 1-27 (1964).
Rugg-Gunn, P. J. et al Nat Genet 37, 585-7 (2005).
Gertow, K. et al. Stem Cells Dev 13, 421-35 (2004).
Evans, M. J. et al Nature 292, 154-6 (1981).
Martin, G. R. Proc Nati Acad Sci USA 78, 7634-8 (1981).
Thomson, J. A. et al. Proc Nati Acad Sci USA 92, 7844-8 (1995)
Thomson, J. A. et al. Biol Reprod 55, 254-9 (1996).
Thomson, J. A. et al. Science 282, 1145-7 (1998).
Daheron, L. et al. Stem Cells 22, 770-8 (2004).
Ying, Q. L. et al. Cell 115, 281-92 (2003).
Xu, R. H. et al. Nat Biotechnol 20, 1261-4 (2002).
Vallier, L. et al. Dev Biol 275, 403-21 (2004).
Vallier, L. et al J Cell Sci 118, 4495-509 (2005).
Beattie, G. M. et al. Stem Cells 23, 489-95 (2005).
James, D. et al Development 132, 1273-82 (2005).
Xu, R. H. et al. Nat Methods 2, 185-90 (2005).
Johansson, B. M. & Wiles, M. V. Mol Cell Biol 15, 141-51 (1995).
Camus, A. Dev Biol 295, 743-55 (2006).
Mesnard, D. et al Development 133, 2497-505 (2006).
Brook, F. A. et al. Diabetes 52, 205-8 (2003).
Matsui, Y., Zsebo, K. & Hogan, B. L. et al Cell 70, 841-7 (1992).
Niwa, H. et al. Nat Genet 24, 372-6 (2000).
Boyer, L. A. et al. Cell 122, 947-56 (2005).
Loh, Y. H. et al. Nat Genet 38, 431-40 (2006).
Meissner, A. & Jaenisch, R Dev Dyn 235, 2460-9 (2006).

The invention claimed is:

1. A method of producing a population of isolated mouse or rat pluripotent Epiblast Stem Cells (EpiSCs) that are substantially free from other cell types, the method comprising the steps of:
    a) obtaining a rat or mouse post-implantation embryo;
    b) isolating the late epiblast layer of the post-implantation embryo and microdissecting it away from extraembryonic tissues;
    c) culturing the microdissected late epiblast layer of step (b) under conditions in which the Activin/Nodal signaling pathway is activated such that a population of isolated mouse or rat pluripotent EpiSCs that are substantially free from other cell types is produced.

2. The method of claim 1 wherein the Activin/Nodal pathway is activated by an Activin/Nodal pathway activator selected from the group consisting of activin A, activin B, activin AB, TGFbeta1, GDF-3 and Nodal.

3. The method of claim 1 wherein the population of isolated mouse or rat pluripotent EpiSCs that are substantially free from other cell types is unresponsive to LIF.

4. The method of claim 1 wherein the population of isolated mouse or rat pluripotent EpiSCs that are substantially free from other cell types express Oct4, Nanog, Sox2, Fgf5 and Nodal and do not express Blimp1, Stella, alkaline phosphatase, Gbx2 or Rex1.

5. The method of claim 1 wherein the mouse or rat pluripotent EpiSCs retain their pluripotency when continuously cultured under conditions in which the Activin/Nodal signaling pathway is activated.

6. The method of claim 1 or 5 which optionally comprises supplementing the culture with FGF2.

\* \* \* \* \*